US012727958B2

(12) United States Patent
Kebel et al.

(10) Patent No.: US 12,727,958 B2
(45) Date of Patent: Sep. 8, 2026

(54) SKIN PACKAGING WITH PROTECTIVE SHEATH

(71) Applicant: Stryker European Operations Limited, Carrigtwohill (IE)

(72) Inventors: Roland Kebel, Wangen an der Aare (CH); Stefan Miehle, Selzach (CH); Theresa Weiger, Selzach (CH); Moritz Oeler, Selzach (CH); Daniel Thran, Selzach (CH)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 19/185,878

(22) Filed: Apr. 22, 2025

(65) Prior Publication Data

US 2025/0325341 A1 Oct. 23, 2025

Related U.S. Application Data

(60) Provisional application No. 63/637,619, filed on Apr. 23, 2024.

(51) Int. Cl.

| | |
|---|---|
| ***A61B 50/30*** | (2016.01) |
| ***B65D 75/30*** | (2006.01) |
| ***B65D 81/20*** | (2006.01) |
| *A61B 50/00* | (2016.01) |

(52) U.S. Cl.

CPC ........ *A61B 50/30* (2016.02); *A61B 2050/002* (2016.02); *A61B 2050/3015* (2016.02); *A61B 2050/316* (2016.02)

(58) Field of Classification Search

CPC .... B65D 75/305; B65D 77/04; B65D 81/203; A61B 50/30; A61B 2050/002; A61B 2050/3015; A61B 2050/314; A61B 2050/316; A61F 2/0095

USPC ...................... 206/363–365, 368, 438, 524.8

See application file for complete search history.

(56) References Cited

U.S. PATENT DOCUMENTS

| | | | |
|---|---|---|---|
| 3,301,392 | A | 1/1967 | Regan, Jr. |
| 4,482,053 | A | 11/1984 | Alpern et al. |
| 5,690,226 | A | 11/1997 | N'Guyen |
| 6,830,149 | B2 | 12/2004 | Merboth et al. |

(Continued)

FOREIGN PATENT DOCUMENTS

| | | | |
|---|---|---|---|
| DE | 4229314 | A1 | 3/1994 |
| EP | 0982236 | B1 | 5/2003 |

(Continued)

OTHER PUBLICATIONS

Extended European Search Report including Written Opinion for Application No. 25171873.0 dated Sep. 1, 2025. 8 pgs.

*Primary Examiner* — Luan K Bui

(74) *Attorney, Agent, or Firm* — Lerner David LLP

(57) ABSTRACT

A package assembly including a sheath, a pouch, and an outer enclosure. The sheath includes perforations that extend across the sheath along an orientation that is transverse to an elongate dimension of the sheath. The sheath is configured to receive and enclose an implant or a surgical instrument. The pouch has an inner volume that receives the sheath, the inner volume of the pouch being configured to be vacuum sealed. The outer enclosure is designed to receive the pouch. The sheath is made of a material with greater rigidity than the pouch.

20 Claims, 19 Drawing Sheets

(56) References Cited

U.S. PATENT DOCUMENTS

| | | | | |
|---|---|---|---|---|
| 6,889,839 | B1 * | 5/2005 | Rosten ................. | B65D 81/075<br>206/583 |
| 7,299,981 | B2 | 11/2007 | Hickle et al. | |
| 8,096,420 | B2 | 1/2012 | Marhsall et al. | |
| 8,113,348 | B2 | 2/2012 | Foster | |
| 8,966,867 | B2 | 3/2015 | Liccardo et al. | |
| 9,789,990 | B2 | 10/2017 | Raming | |
| 10,299,877 | B2 | 5/2019 | Volk et al. | |
| 11,627,617 | B2 | 4/2023 | Daniels | |
| 2003/0121811 | A1 * | 7/2003 | Roshdy .................. | A61B 50/30<br>206/363 |
| 2003/0168370 | A1 * | 9/2003 | Merboth ............... | A61F 2/0095<br>206/438 |
| 2006/0243616 | A1 | 11/2006 | Caron | |
| 2007/0209957 | A1 | 9/2007 | Glenn et al. | |
| 2007/0287976 | A1 * | 12/2007 | Sherrill ................. | A61F 15/001<br>604/385.06 |
| 2012/0205269 | A1 * | 8/2012 | Ludvig .................. | A61B 50/30<br>206/363 |
| 2014/0299498 | A1 * | 10/2014 | Neal ......................... | A61J 1/00<br>53/473 |
| 2018/0222655 | A1 | 8/2018 | Grabowski et al. | |
| 2021/0229887 | A1 * | 7/2021 | Hughes .................. | B65D 77/26 |

FOREIGN PATENT DOCUMENTS

| | | | |
|---|---|---|---|
| EP | 4030410 | A1 | 7/2022 |
| WO | 2023064448 | A1 | 4/2023 |

* cited by examiner

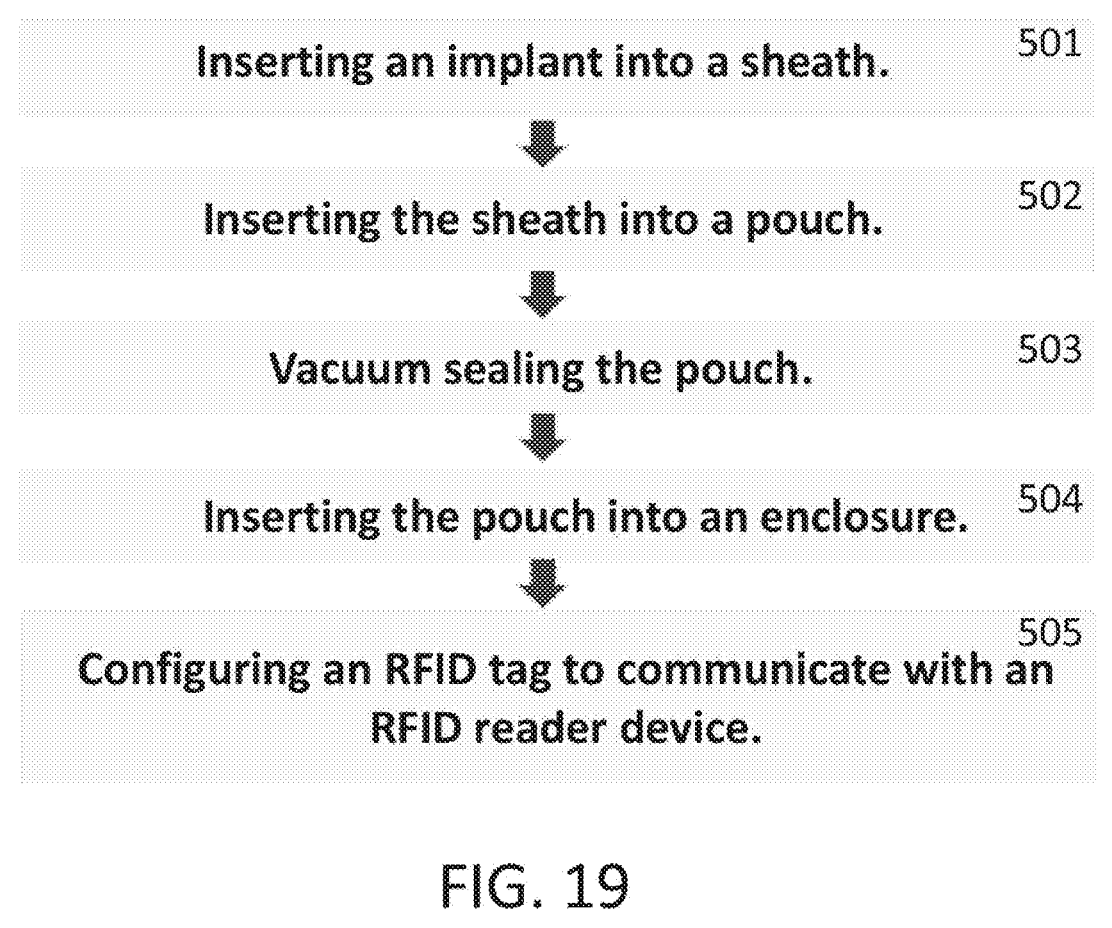

Inserting an implant into a sheath. 501

Inserting the sheath into a pouch. 502

Vacuum sealing the pouch. 503

Inserting the pouch into an enclosure. 504

Configuring an RFID tag to communicate with an RFID reader device. 505

FIG. 19

SKIN PACKAGING WITH PROTECTIVE SHEATH

CROSS-REFERENCE TO RELATED APPLICATIONS

The present application claims priority to U.S. Provisional Application No. 63/637,619 filed Apr. 23, 2024, the contents of which are incorporated herein by reference.

BACKGROUND

Medical devices such as implants, implant trials, prostheses, surgical instruments, and the like are ubiquitous in contemporary medical procedures. Such medical devices are typically packaged for shipment and storage before being deployed in a medical procedure. Packaging for such medical devices is generally designed to provide protection for a device and in some cases maintain the sterility of the device. To accomplish this, various arrangements have been developed, often requiring a complex combination of components and/or bulky components. Additionally, product information is often provided through user manuals, product information packets, and/or product labels that are difficult to fit into and/or place on the packaging and are otherwise difficult to include without the consumption of a significant amount of material and the provision of a large volume of storage space.

Accordingly, there is a need for packaging that securely stores sterile or non-sterile devices and allows for simple and rapid retrieval of the medical device from the packaging, while also being sustainable through an efficient use and arrangement of materials.

BRIEF SUMMARY

In a first aspect, the present disclosure relates to a package assembly that, among other features, reduces the material used for packaging medical implants and instruments while still providing adequate protective layer and a sterile barrier layer. The sterile barrier layer may include a sterile pouch, a sheath, a pre-formed blister and other protective layers. The sterile pouch may include an enclosure with pull tabs extending from the top end and an opening into the enclosure at the bottom end. The sheath may have two rounded edges with an opening at one end designed such that an implant or medical instrument can be inserted into the sheath via the opening. The sheath may be made from a firmer material than the sterile pouch and is small enough to fit within the enclosure of the sterile pouch. The sterile pouch may be sealed in a manner such that the sheath disposed in the pouch may be immovable with respect to the pouch.

The protective barrier layer is designed to house an implant or instrument enclosed in a non-sterile or sterile barrier layer. The protective barrier layer generally includes an outer package that may comprise only one unit, e.g., a box, or multiple components that attach together to form a protective barrier. One example of a multi-component outer package includes a firm layer and a flexible layer, the flexible layer configured cover an implant or instrument in a sterile barrier layer that is placed on the firm layer such that a seal is formed around the sterile barrier layer to secure it to the firm layer.

The protective and sterile barrier layers also include features that facilitate retrieval of the implant or instrument contained therein. For example, in the case of the multi-component protective barrier layer, the flexible layer may have a loose corner that extends beyond a slanted edge of the firm layer to form a peel tab. This peel tab provides a convenient way for medical personnel, who may be wearing latex gloves, to separate the flexible layer from the firm layer by grabbing and pulling the loose corner. As for the sterile barrier layer, the sterile pouch has two pull tabs that, when pulled in opposite directions, pull apart the seal surrounding the sheath contained in the enclosure of the pouch. Additionally, the sheath has perforations extending between two recesses positioned on opposite sides of the sheath. The perforations and recesses define a tear line such that the sheath can be torn into two pieces to facilitate the removal the implant or instrument from the sheath.

In a second aspect, the present disclosure relates to a package having a sheath, a pouch, and an outer enclosure. The sheath may have perforations extending across a width of the sheath such that the perforations are transverse to an elongate dimension of the sheath. The sheath may be configured to receive and enclose an implant or a surgical instrument. The pouch may have an inner volume receiving the sheath therein, and the inner volume of the pouch may be configured to be vacuum sealed. The outer enclosure may be configured to receive the pouch. The sheath may have a first rigidity, and the pouch may have a second rigidity less than the first rigidity. In such instances, the sheath may have a thickness in a range from 0.5 mm to 3.0 mm. In other instances, the outer enclosure may include a backing board and a film that are sealed together with a seal that extends around the pouch disposed between the backing board and the film. The seal may be formed through heat connecting the film onto the board. The backing board may be paperboard. The backing board may include a first layer and a second layer, and each layer may be substantially planar. The first layer may include an information card that is at least partially detachable from the second layer.

The package may further comprise a radio frequency identification (RFID) tag on the first layer. The RFID Tag may be a passive RFID tag. The first layer may be joined to a remainder of the plurality of planar layers via a line of perforations that define an outer perimeter of the first layer. A top layer and a bottom layer of the sheath may be unattached at one end of the sheath, such unattached end defining an opening. The pouch may be made of polyethylene (PE) film, Tyvek® film, or polyamide (PA) film. The pouch may include two film layers attached together with a peelable seal. The film may include a peel tab that extends beyond an edge of the backing board. The outer enclosure may be a box and a film wrapped around the box.

In accordance with another aspect, the present disclosure relates to a system for packaging an object for use in surgery that may include a sheath, an object, and a pouch. The sheath may have an enclosed pocket with the object disposable therein, the sheath having a line of perforations extending from a first side of the enclosed pocket to a second side of the enclosed pocket opposite the first side. The pouch may enclose the sheath and the implant, and the pouch may have a vacuum sealed periphery including a sealed portion with an apex shape configured to be peeled open. The sheath may have a first thickness, and the pouch may have a second thickness less than the first thickness. The sheath may include an elongate dimension extending from a first end to a second end and the first and second ends both have a rounded shape. The enclosed pocket may be defined by two layers of the sheath, and one layer of the two layers may have a cutout at one end of an elongate dimension of the sheath to define a tab for separating the two layers. The sheath may include a first recess along the first side and a second recess along the second side, each of the first and second recesses may be positioned adjacent to respective ends of the line of perforations extending across the enclosed pocket. The first and second recesses may be V-shaped.

The system for packaging an object for surgery may further comprise an outer package and a radio frequency identification (RFID) tag configured to wirelessly transmit shipping and/or storage information such that the RFID tag is attached to the outer package. The system may further comprise a folding box enclosing the pouch, wherein the folding box includes an end-panel label. The system may further comprise a patient record label disposed within the folding box. The sheath and the pouch may be translucent. The object may be an implant or a surgical instrument.

In accordance with another aspect, the present disclosure relates to a process of packaging an implant. This process may include an implant inserted into a sheath having perforations extending across a width of the sheath between two recesses disposed on opposite sides of the sheath. After such insertion, the sheath and the implant may be inserted into a pouch. The pouch may be vacuum sealed. After such sealing, the pouch may be inserted into an outer enclosure. The process may further comprise an outer enclosure that is shrink wrapped with shrink wrap film, and the outer enclosure may be a folding box. The process may further include a radio frequency identification (RFID) tag on the outer enclosure that may be configured to include information about the implant.

In accordance with another aspect, the present disclosure relates to a process of unpacking a medical object. This process may include a pouch retrieved from within an inner chamber. The inner chamber may contain a sheath, and the pouch may define a sterile barrier around the sheath. After such retrieval, a first layer of a pouch may be peeled away from a second layer of the pouch. Then the sheath may be extracted from the pouch. After such extraction, the sheath may be torn along a line of perforations extending across a width of the sheath to partially expose the medical object, and the medical object may be removed from within the sheath. The process of unpacking may further comprise the pouch being removed from an outer enclosure. The pouch may be removed from the outer enclosure by pulling a peel tab to separate a flexible film of the outer enclosure from a backing board of the outer enclosure. The process of unpacking may further comprise shrink wrap film of the outer enclosure being torn from a box of the outer enclosure.

BRIEF DESCRIPTION OF THE DRAWINGS

A more complete appreciation of the subject matter of the present disclosure and the various advantages thereof may be realized by reference to the following detailed description which refers to the accompanying drawings, in which:

FIG. 19 is a flow chart of the process for packaging an implant within a package assembly according to an embodiment of the present disclosure;

DETAILED DESCRIPTION

While the present disclosure will now be described in detail with reference to the figures, it is done so in connection with the illustrative embodiments but is not limited by the particular embodiments illustrated in the figures.

As used herein unless stated otherwise, the terms "about," "generally," and "substantially" are intended to mean that slight deviations from absolute are included within the scope of the term so modified.

The present disclosure relates to package assemblies, kits including one or more components of such package assemblies, and various methods associated therewith. Kits may include any combination and/or number of packaging components as contemplated herein. Methods may include methods of packaging items such as medical implants or instruments. Examples of implants or instruments packaged through such methods include, but are not limited to, bone screws, bone plates, intramedullary nails, joint prostheses, implant trials, needles, sutures, medical instruments, etc.

Other methods include methods of opening a package assembly. The package assemblies are modular in that different versions of one component are compatible with a single set of the remaining components. Thus, in one non-limiting example, different sheaths may be used with a single pouch and outer packaging. The package assembly can be used to package any variety of medical implants, medical instruments, or non-medical items in a manner that reduces waste, storage space, and packaging time. With regard to the packaging assemblies described herein, the term outer packaging may be used as general term for a base and a film sealed together, e.g., a backing board and a film sealed together, or a box, among other enclosures having a similar function.

Figure 1:
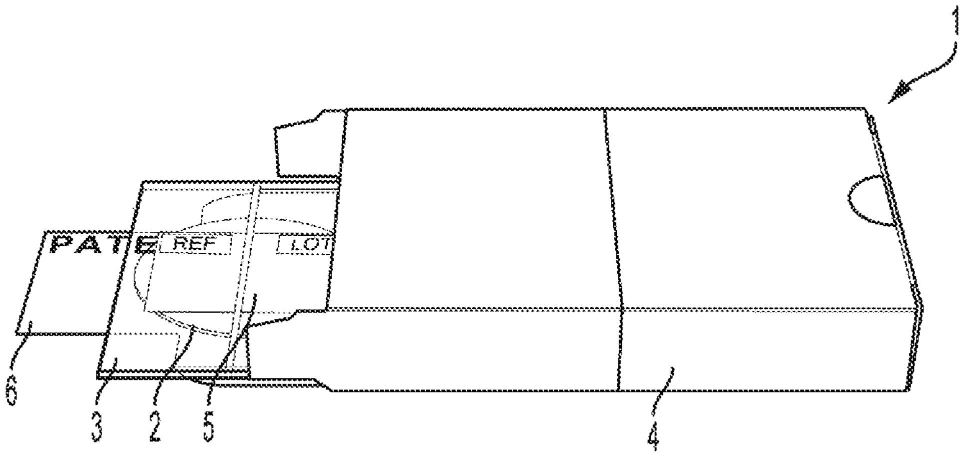
FIG. 1 is a perspective view of a package assembly according to an embodiment of present disclosure.
Figure 2:
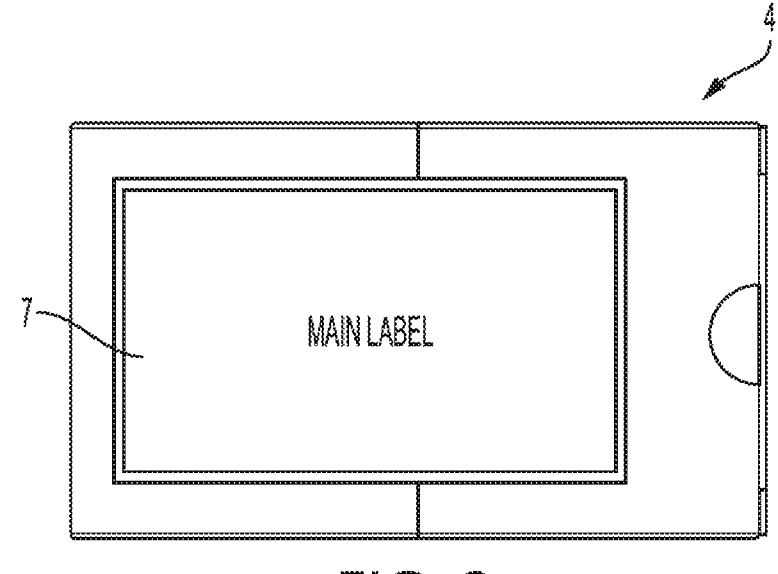
FIG. 2 is a top view of the package assembly of FIG. 1.
Figure 3:
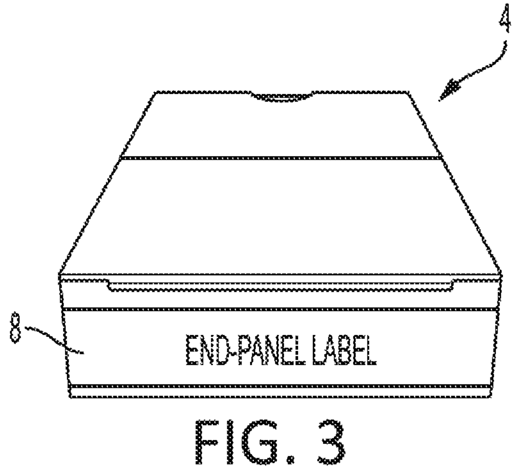
FIG. 3 is a side view of the package assembly of FIG. 1.
Figure 7:
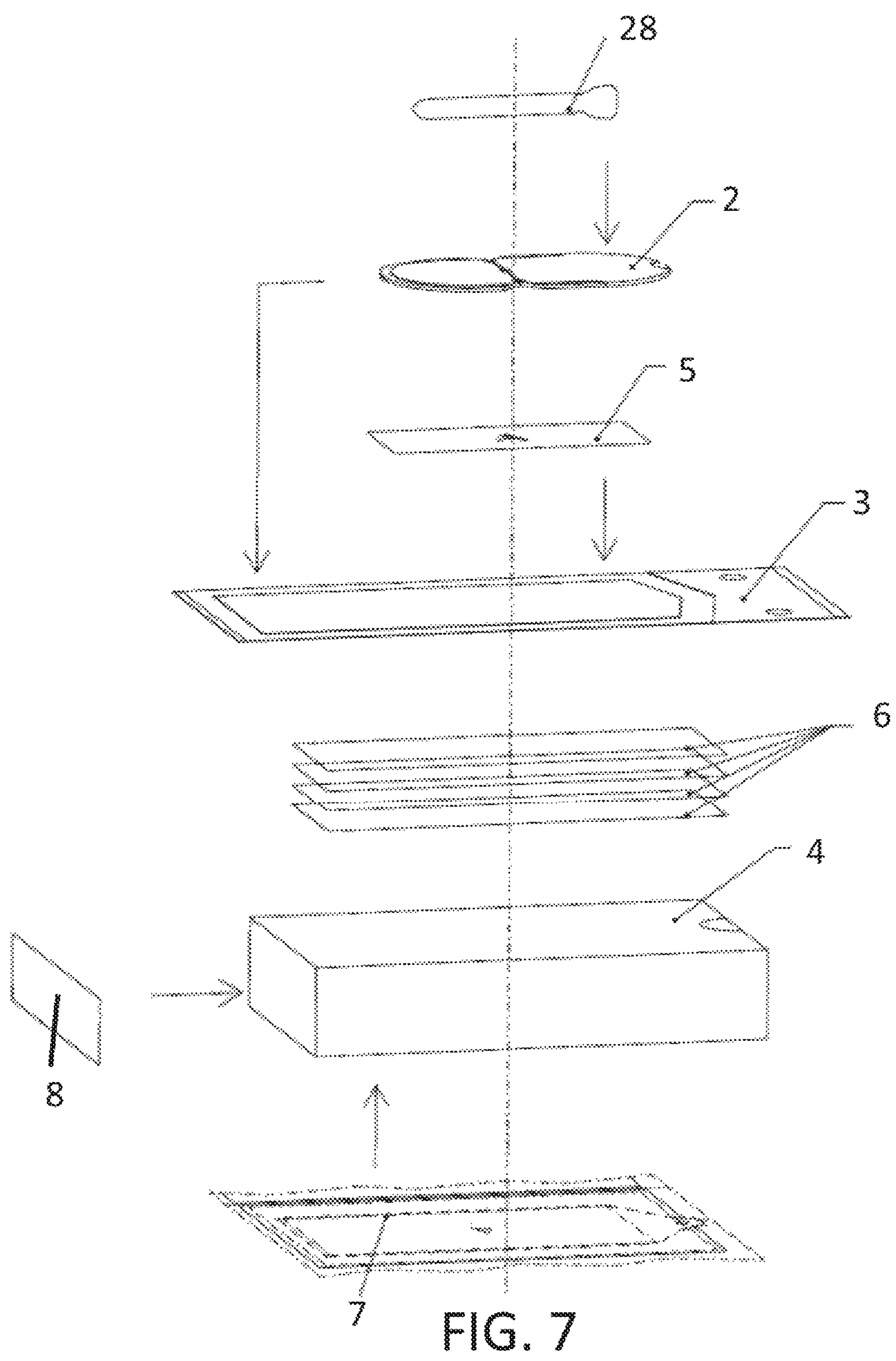
FIG. 7 is an exploded view of the package assembly of FIG. 1.
Figure 8:
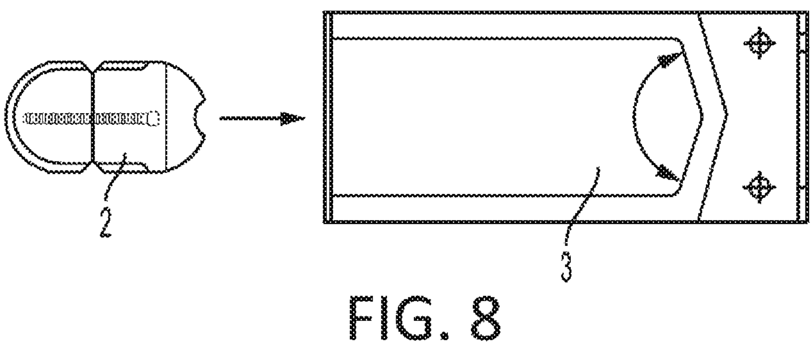
FIG. 8 illustrates a sheath insertion step in a method of assembling a package assembly according to an embodiment of the present disclosure.

In one aspect, the present disclosure relates to package assemblies. One embodiment of a package assembly is package assembly 1 shown in FIGS. 1 and 7. In an assembled condition, package assembly 1 includes a box 4 housing an implant, e.g., fastener 28 shown in FIG. 5, a sheath 2, a pouch 3, and, optionally, documents 6. Documents included in the package assembly may be one or more of patient records, implant or instrument records, user instructions, and other documents related to the contents of the package. Implant 28, sheath 2 and pouch 3 are arranged in a particular manner within box 4. Specifically, the implant is disposed within sheath 2, and sheath 2 is vacuum sealed within pouch 3. As shown in FIGS. 1 and 7, an optional product label 5 is affixed to pouch 3. As depicted, box 4 is a folding box with openable panels on opposing ends of the box, as shown in FIGS. 1-3, and may include a main label 7 and/or an end-panel label 8 that have additional information printed thereon regarding the contents of the box, e.g., product type, dimensions, material, shipping or storage information. While FIGS. 1-3 show box 4 with long and narrow dimensions, the box may have much larger or smaller dimensions to accommodate larger or smaller implants or surgical instruments. In some variations, main label 7 may be a multi-layer label, such as the multi-layer labels described in U.S. Pat. No. 11,776,431, the entire disclosure of which is hereby incorporated by reference herein in its entirety.

Figure 4:
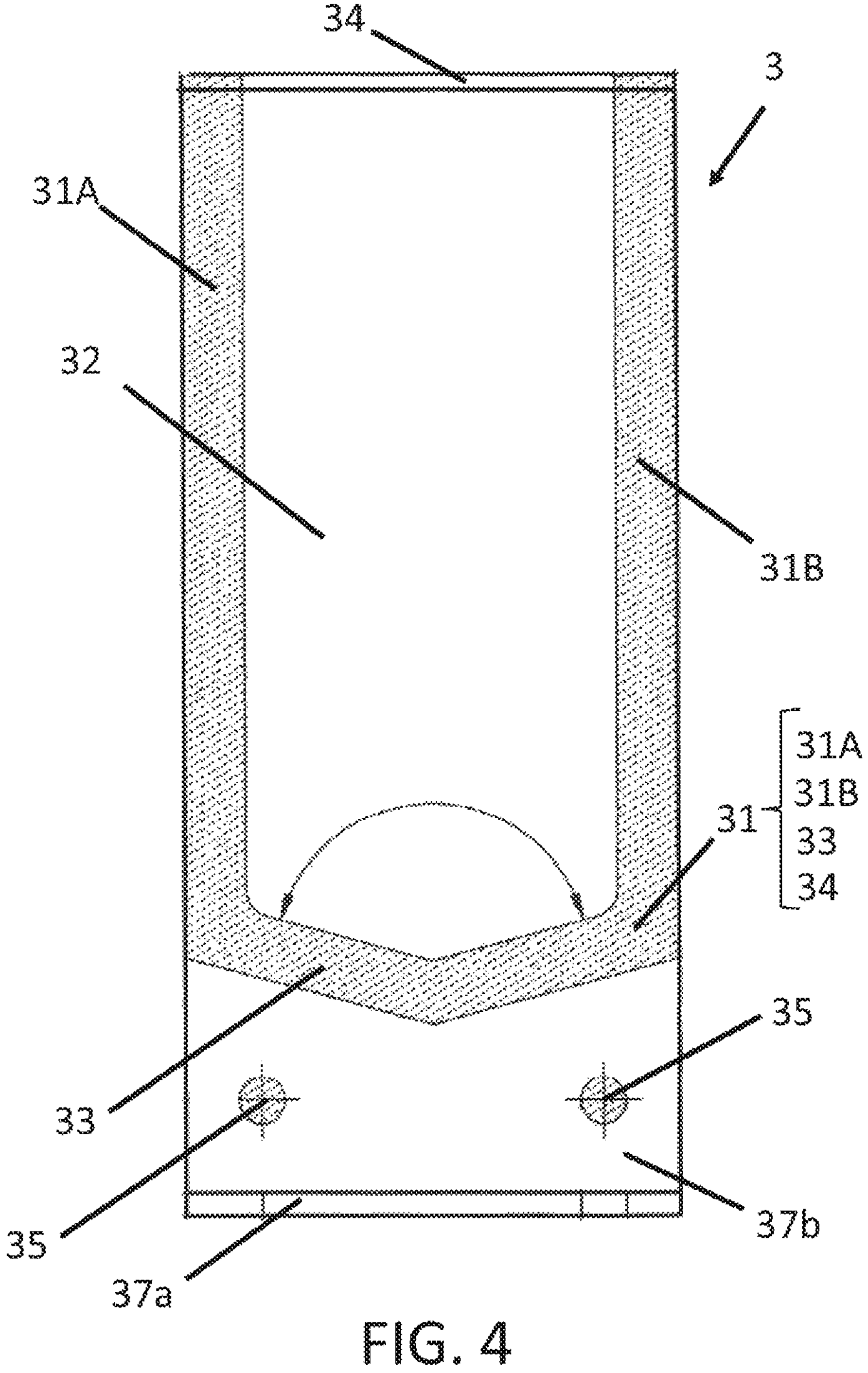
FIG. 4 is a top view of a vacuum sealed pouch included in the package assembly of FIG. 1.
Figure 9:
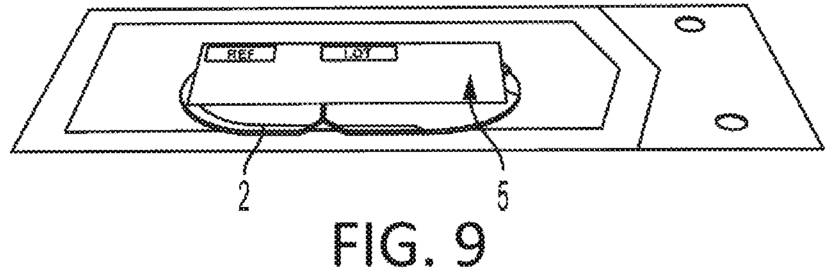
FIG. 9 illustrates a labeling step in the method of FIG. 8.
Figure 10:
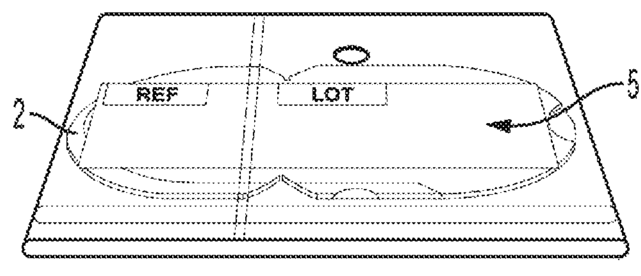
FIG. 10 illustrates a pouch folding step in the method of FIG. 8.
Figure 11:
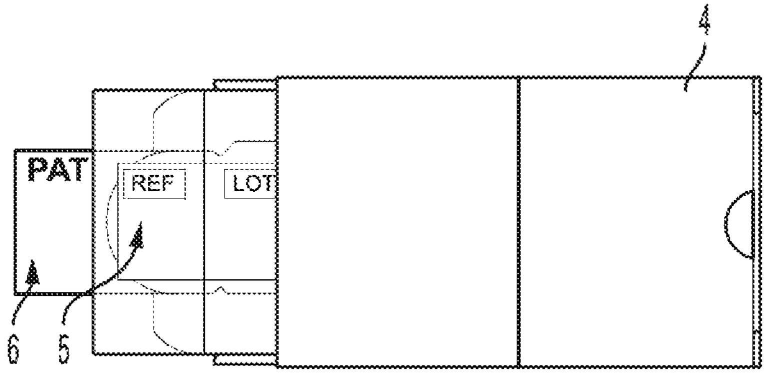
FIG. 11 illustrates a pouch and label insertion step in the method of FIG. 8.

Turning to the details of pouch 3, as shown in FIG. 4, pouch 3 includes two layers of film attached together such that an inner chamber 32 is defined therebetween. The layers of the two-layer film may be the same or different materials, and the material(s) of the film layers of pouch 3 are discussed in more detail below. Inner chamber 32 of pouch 3 is designed to receive sheath 2 and create a sterile or non-sterile barrier around the sheath and the implant once the pouch has been vacuum sealed. Pouch 3 includes a seal 31 that extends around and encloses inner chamber 32 of the pouch, the seal being designed to hold together the two layers that are joined along a periphery of the inner chamber of the pouch. Seal 31 includes a series of segments to form the periphery of the inner chamber, including side portions 31A, 31B, end portion 34 extending between the side portions at a first end of pouch 3, and an angled portion 33 in the shape of a chevron symbol remote from the first end, angled portion 33 also extending between the side portions. When prepared, packaged and ready for use, end portion 34 and side portions 31A, 31B are sealed closed, along with angled portion 33. Pouch 3 is configured to allow for retrieval of an object sealed within inner chamber 32 through angled portion 33. Angled portion 33 and side portions 31A and 31B are a peelable seal and allow for the extraction of an object within the inner chamber, such as sheath 2, which is discussed in greater detail below. Prior to pouch 3 being vacuum sealed, there is an opening into inner chamber 32 at the location of end portion 34 through which an implant or instrument may be inserted. Formation of end portion 34 is discussed in more detail below. As depicted in FIG. 9, seal 31 completely surrounds the contents in inner chamber 32 with end portion 34 of the seal being the last portion of the seal that is formed. Pouch 3 is advantageous in that when inner chamber 32 is sealed, the pouch forms a barrier to maintain cleanliness and the sterility of any contents within the inner chamber, such as an implant or instrument disposed within a sheath that is further disposed in the inner chamber. Such sterility may further be maintained during shipping and storage.

As mentioned above, pouch 3 is formed from two layers of film. Respective ends of each layer proximate angled portion 33 of the seal and external to inner chamber 32 define pull tabs 37*a*, 37*b*. Also external to the inner chamber 32, pouch 3 includes a pair of safety seals 35 that hold together pull tabs 37*a*, 37*b*, as shown in FIG. 4. In this manner, safety seals 35 maintain an attachment between the layers of the pouch and prevent the angled portion of the seal from being broken by an accidental separation of pull tabs 37*a*, 37*b* during shipping and storage. Safety seals 35 and seal 31 may be made of polymeric material melted together or adhered together with an adhesive. During manufacture, seals 31, 35 may optionally be formed together in a single step.

Figure 5:
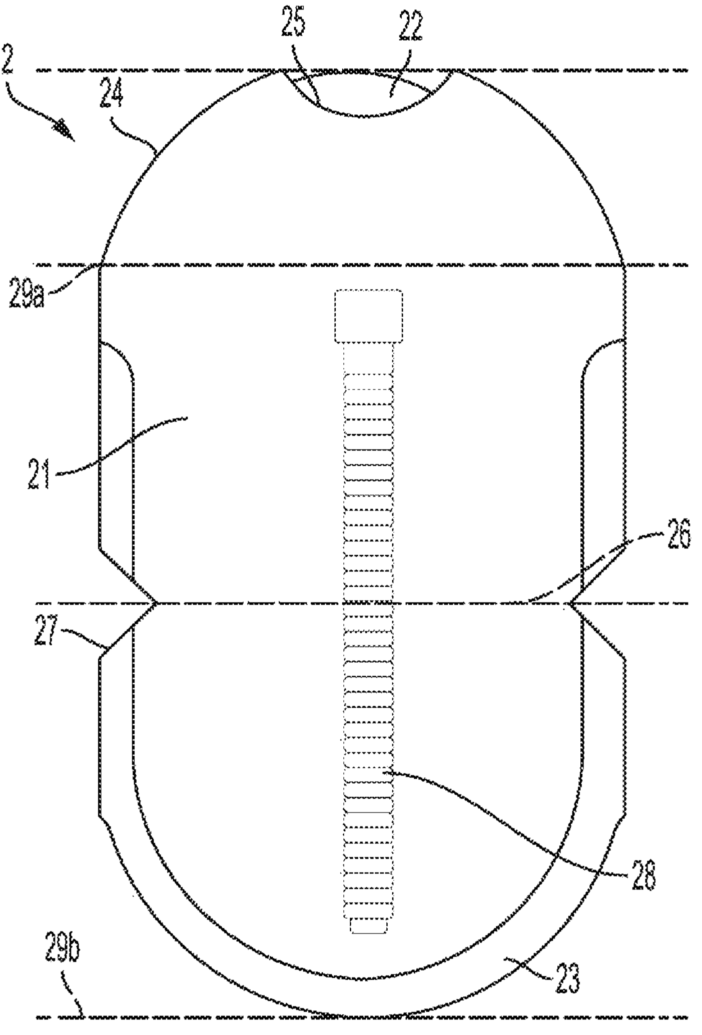
FIG. 5 is a top view of a sheath included in the package assembly of FIG. 1.

As to sheath 2, as shown in FIG. 5, sheath 2 is designed to encase a surgical instrument or medical implant within a semi-rigid covering, i.e., more rigid than pouch 3, to protect an implant or instrument encased therein and to prevent the implant or instrument from piercing the walls of inner chamber 32 of pouch 3. Sheath 2 has top layer 21 and a bottom 22 layer that are attached (e.g., welded or melted) together along a sealed portion 23 and are unattached along an unsealed portion 24, the unsealed portion defining an opening by which an implant or instrument may be inserted into the sheath. In some examples, dimensions of the surfaces of top and bottom layers 21, 22 that face each other may be similar or the same. One such example is shown in FIG. 5, where sealed portion 23 around a portion of the periphery of pouch 3 holds top and bottom layers 21, 22 together. Top layer 21 has a crescent cutout 25 along unsealed portion 24 to aid in spreading apart top layer 21 and bottom layer 22 by exposing a portion of the bottom layer such that it may be gripped during use. Sheath 2 also includes two V-shaped recesses 27 on opposite sides of the sheath and a series of perforations 26 extending across a distance between the recesses. In FIG. 5, perforations 26 are shown along top layer 21. However, it should be appreciated that such perforations may be along either top layer 21, bottom layer 22, or along both the top layer and the bottom layer. In sheath 2 as depicted, the line of perforations is orthogonal to a length of sheath and is located slightly closer to an end of sheath opposite crescent cutout 25. In variations, a location of the line of perforations relative to end portion 34 may vary from that shown. Further, in some variations, an angulation of the perforations and/or a location of the perforations along a length of the sheath may vary from that shown in FIG. 5. For example, and as described further below, sheath 602, 802 in FIGS. 6A and 6B includes a line of perforations proportionally closer to the tab than the perforations of sheath 2.

As to materials, sheath 2 is made from a material more rigid than the film layers of pouch 3 and both opposing ends of sheath 2 are rounded. One advantage of the rounded ends of sheath 2 is that it reduces the risk that the sheath may puncture a hole in the walls of the pouch when it is disposed within the pouch and thereby damage the sterile barrier of package assembly 1. Another advantage of the sheath structure is that it protects any object enclosed within the sheath, such as implant 28, from external impacts, such as those that may occur during shipping. Optionally, the edges of the sheath may have a different contour. Additionally, sheath 2 may be made from material that is transparent or translucent such that an implant or instrument packaged within the sheath is visible from the outside. In this manner, the contents of package assembly 1 can be confirmed without opening or compromising the sterile barrier created by the vacuum sealed pouch.

With continued reference to sheath 2, sheath 2 includes features that facilitate easy extraction of an implant or instrument from within the sheath. For instance, V-shaped recesses 27 and perforations 26 on sheath 2 provide a tear line that can be used for splitting the sheath to more easily remove the implant from within the sheath. In this manner, medical personnel wearing surgical gloves and gear can readily remove an implant or instrument packaged within sheath 2. Sheath 2 may be made from a variety of polymers. For example, contemplated polymers include, but are not limited to, any type of thermoplastic polyurethane (TPU). The sheath may be formed to have a stiffness greater than the film layers of pouch 3.

Figures 6A, 6B:
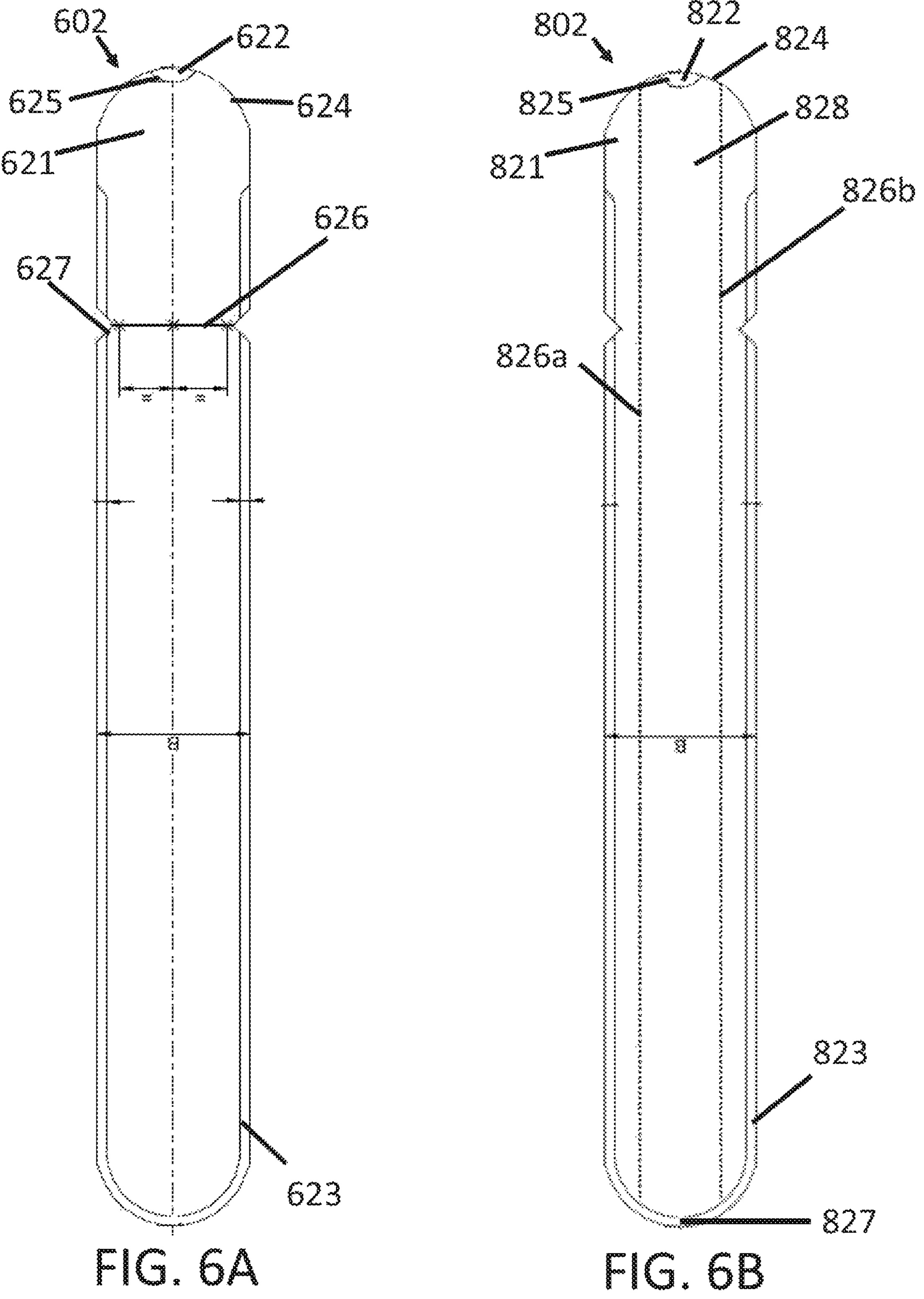
FIG. 6A is a top view of a sheath according to an embodiment of the present disclosure.
FIG. 6B is a top view of a sheath according to an embodiment of the present disclosure.

In another embodiment, sheath 602 is as shown in FIG. 6A. In FIG. 6A, the 600-series of reference numerals refer to like elements of the single or double-digit series of reference numerals in sheath 2 of FIG. 5, unless otherwise noted. Sheath 602 has the same V-shaped recesses 627 positioned on opposite sides of the sheath with perforations 626 running therebetween. Also, sheath 602 has a crescent cutout 625 at an unsealed portion 624 of the sheath. The shape and dimensions of the sheath may be customized to correspond to the shape and size of a specific implant or surgical tool. While the corresponding figures show only one sheath vacuum sealed within a pouch, it is contemplated that multiple sheaths may be vacuum sealed within the same sterilized pouch. Additionally, it is contemplated that sheath 2 may be designed to enclose multiple implants, instruments, or implant assemblies.

In another embodiment, as shown in FIG. 6B, a pair perforated tear lines 826*a*, 826*b* extend along the length of sheath 802 from unsealed portion 824 toward end 827 on the opposite side of the sheath and define a central segment 828. In FIG. 6B, the 800-series of reference numerals refer to like elements of the single or double-digit series of reference numerals in sheath 2 of FIG. 5, unless otherwise noted. Perforated tear lines 826*a*, 826*b* run parallel to each other on upper layer 821 and are disposed on opposite sides of crescent cutout 825 such that an implant or instrument can be positioned between the perforated tear lines when disposed within sheath 802, i.e. in the pocket defined by the upper and lower layers of the sheath 821, 822. In this manner, the implant or instrument can be released from sheath 802 by pulling crescent cutout 825 toward end 827 to tear perforated tear lines 826*a*, 826*b* and separate central segment 828 from upper layer 821 of the sheath.

The inclusion of the perforations in the contemplated sheaths may be varied in many ways. In some embodiments, perforated tear lines 26, 626, 826*a-b* of sheath 2, 602, 802 may be included on a single layer and may be on the upper layer or the lower layer. In other embodiments, perforated tear lines 26, 626, 826*a-b* may be on both the upper and lower layers of the sheath.

In other embodiments, the sheath used in a package assembly may be come in a variety of sizes and shapes but still include the same functional features. For example, the sheath may have a length in a range from 70 mm to 550 mm. In some examples, a width of the sheath may be in a range from 30 mm to 55 mm. And, in some examples, an overall thickness of the sheath may be in a range from 0.5 mm to 3.0 mm. In still further examples, one or more of the length, width and thickness may be outside of the above ranges. A shape of the sheath may also vary. In some examples, a sheath may be oval, rectangular, triangular, etc. In other variations, the sheath may include a line of perforations extending across a width of the sheath at an oblique angle relative to a length of the sheath. In other examples, the sheath may include one or more pull tab(s) extending from an edge or adjacent edges at the open end (e.g., unsealed portion 24) of the sheath to aid in spreading apart top layer 21 and bottom layer 22 when inserting an implant or instrument into the sheath. In still further examples, the sheath may include multiple peripheral recesses or recesses having a concave shape.

Figure 14:
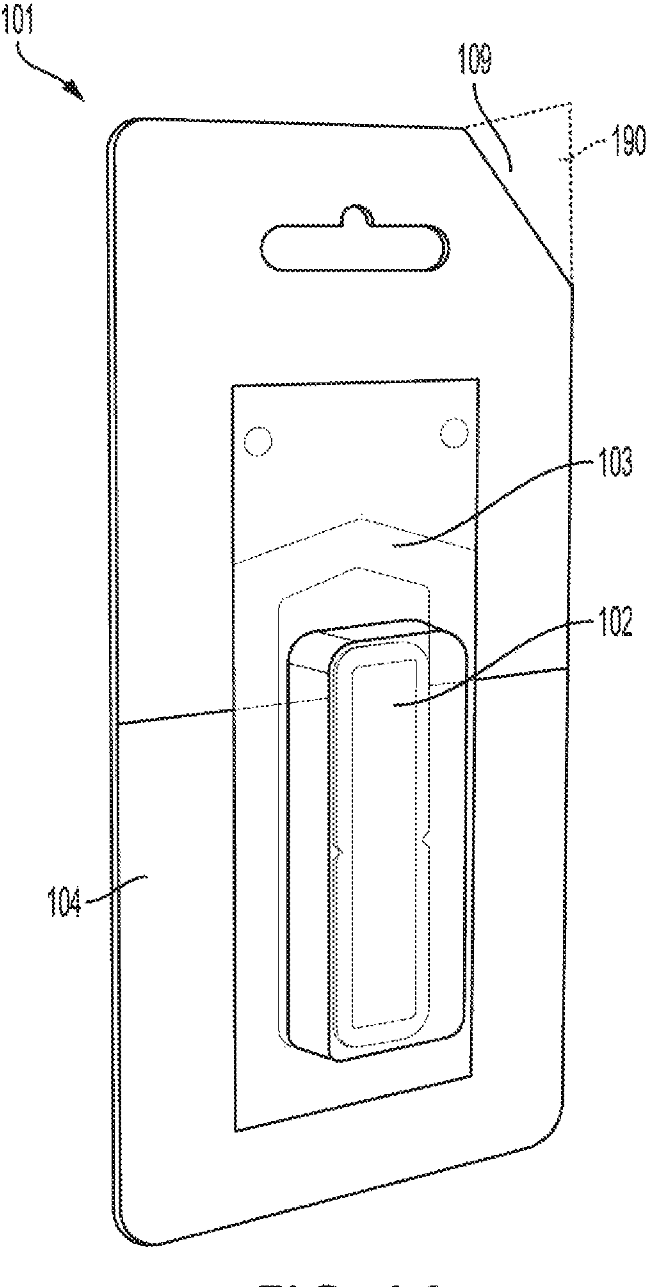
FIG. 14 is a perspective view of a package assembly according to an embodiment of the present disclosure.
Figure 15:
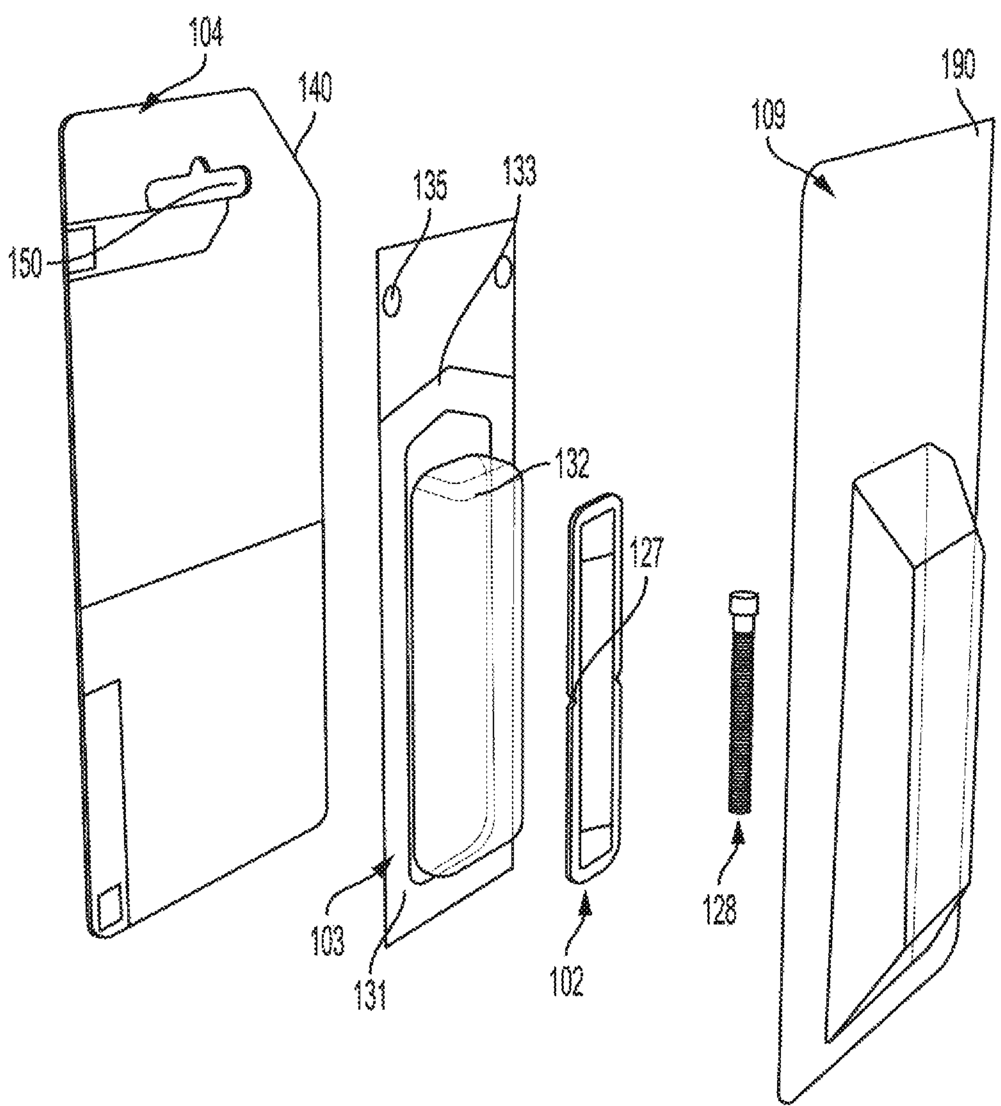
FIG. 15 is an exploded view of the package assembly of FIG. 14.

In another embodiment, as shown in FIGS. 14-15, a package assembly 101 includes a sheath 102 enclosing an implant or instrument, a vacuum sealed pouch 103 enclosing the sheath, and a base 104. Base 104 and a flexible film 109 are sealed together around the pouch. In FIGS. 14-15, the 100-series of reference numerals refer to like elements of the single or double-digit series of reference numerals in sheath 2 of FIGS. 4-7, unless otherwise noted. Flexible film 109 is transparent and is deformable as desired, e.g., to place the film over the pouch. In variations of package assembly 101, an assembly may include a blister as a sterile barrier in place of pouch 103. Examples of film that may be utilized as flexible film 109 include Surlyn® Skin Packaging Film made from DuPont™ Surlyn® resin or some type of skin foil. Flexible film 109 provides a protective layer for pouch 103 during shipping and storage. Flexible film 109 may extend beyond an edge of base 104 at at least one location of base 104 to define a peel tab 190. In this manner, medical personnel can securely grip the flexible film at peel tab 190 to separate the flexible film from the base. In some examples, base 104 may be a backing board in the form of paperboard or cardboard. In some examples, base 104 may be a planar or substantially planar structure made from a rigid material such as, but not limited to, paper-based materials, paper-fiber materials, fiber-based materials, or plastic. Base 104 may have a thickness commensurate with the material used to provide sufficient rigidity to withstand deformation during expected shipping conditions. In other embodiments, package assembly 101 may be disposed within a box, e.g., box 4 of assembly 1, to provide further protection which may be needed when packaging large, heavy items.

Figure 20:
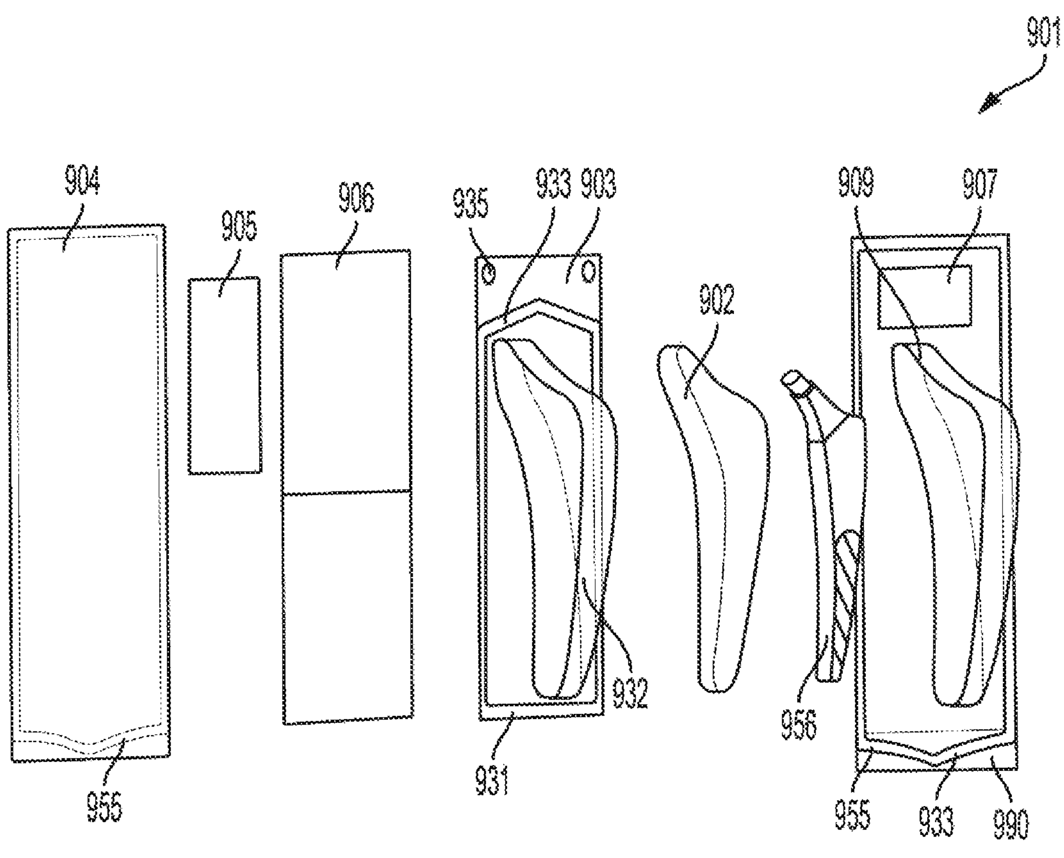
FIG. 20 is an exploded view of a package assembly in accordance with an embodiment of the present disclosure.

In yet another embodiment, as shown in FIG. 20, a package assembly 901 includes a sheath 902 enclosing an implant or instrument, a vacuum sealed pouch 903 enclosing the sheath, and a flexible film base 904. Flexible film base 904 and a flexible film 909 are sealed together around the pouch 903 by a seal 955. In FIG. 20, the 900-series of reference numerals refer to like elements of the single, double, and triple-digit series of reference numerals for sheath 2 and 102, pouch 3 and 103, documents 6, main label 7 and product label 8 shown in FIGS. 1-7 and 14-15, respectively, unless otherwise noted. Flexible film 909 and flexible film base 904 are transparent and deformable as desired such they can be formed to define a cavity or formed to seal off an opening to a cavity to create a sealed pouch.

In variations of package assembly 901, an assembly may include a blister as a sterile barrier in place of or in addition to pouch 903. In other instances, package assembly 901 may include a cardboard insert, e.g., base 104, that is placed between flexible film 909 and flexible film base 905 to add rigidity to the package assembly. Examples of film that may be utilized as flexible film 909 and/or flexible film base 904 include Surlyn® Skin Packaging Film made from DuPont™ Surlyn® resin and/or some type of skin foil. Flexible film base 904 may have a thickness that is greater than or equal to that of the flexible film 909. Flexible film 109 and flexible film base 904 are sealed together via seal 955 to provide a protective layer for pouch 903 during shipping and storage of packaged item or items, e.g., implant 956. Seal 955 may include an angled portion 933 similar to angled portion 33 described above to facilitate separation of the two films. Flexible film 909 and flexible film base 904 may extend beyond seal 955 at at least one location to define a peel tab 990. In this manner, medical personnel can securely grip the flexible film at peel tab 990 to separate the flexible film 909 from the flexible film base 904. In other embodiments, package assembly 901 may be disposed within a box, e.g., box 4 of assembly 1, to provide further protection which may be needed when packaging large, heavy items.

Figure 24:
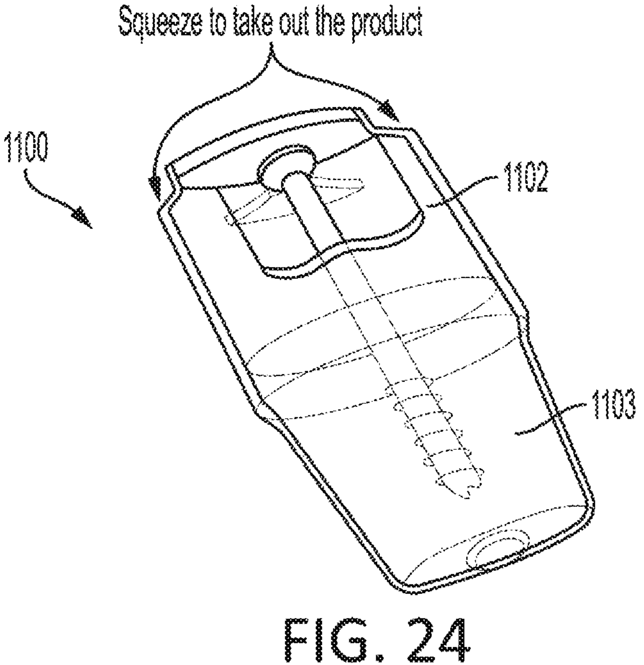
FIG. 24 is a perspective view of the packaging components of FIG. 23.
Figure 25:
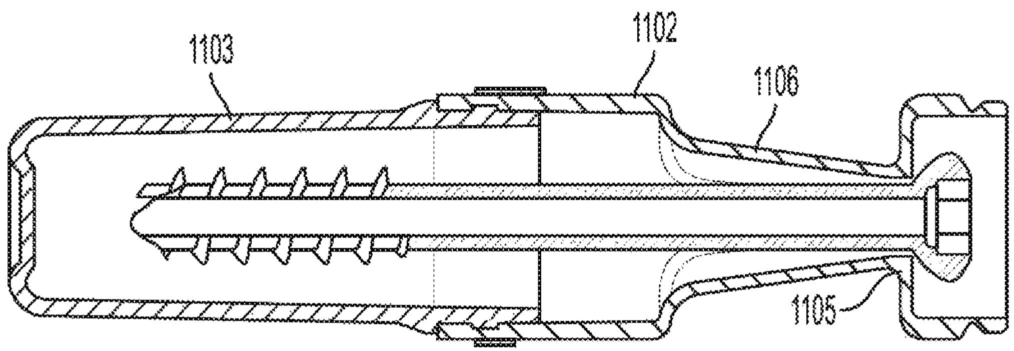
FIG. 25 is a cross-sectional view of the packaging components of FIG. 23.

In some other embodiments, the package assemblies described herein may include a carrier 1100, as shown in FIGS. 23-26, as an alternative to the sheath shown in FIG. 5. The carrier 1100 is designed as a protective packaging element to be used within a sterile barrier to protect the sterile barrier from any sharp or pointed geometries of the packaged item(s) and to protect any critical features of the packaged item, e.g., a medical device, during shipping and storage. The carrier 1100 consists of a cap component 1102 and a sleeve component 1103 configured to be attached to each other, e.g., threaded, clipped, latched, etc., and may be formed via injection molding techniques. The design features of the cap component 1102 may include a screw mount element 1105 that is adapted to fixate a screw head, as shown in FIG. 25, by having a tapered formation 1106 that narrows around the neck of a screw just beneath the screwhead. In this manner, the screw mount element 1105 may be tightly fitted around a screw such that the cap component 1102 may be used to hold the screwhead portion of the screw, without the user making direct contact therewith, while removing the shaft of the screw from the sleeve component 1103 when extracting the screw from the carrier 1100. The screwhead may be released from the screw mount element 1105 by pinching or squeezing the sides of the screw mount element as shown in FIG. 24.

Figure 26:
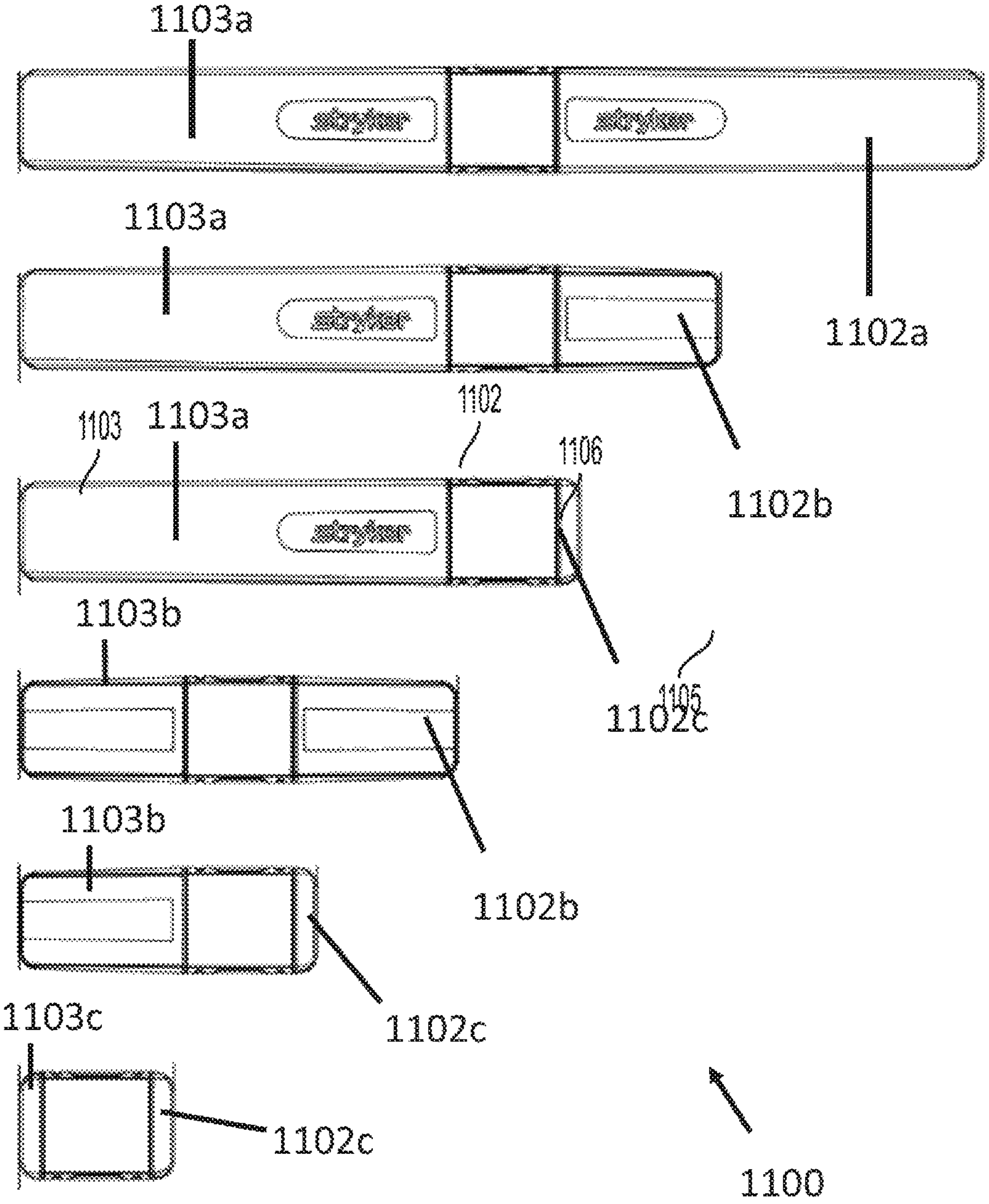
FIG. 26 illustrates various packaging components in accordance with various embodiments of the present disclosure.

The cap component 1102 and the sleeve component 1103 may include different sizes and shapes based on the size and shape of the packaged item. For example, FIG. 26 shows a variety of sizes of these components of the carrier 1100 such as small cap 1102*c* and sleeve 1103*c*, medium cap 1102*b* and sleeve 1103*b*, and large cap 1102*a* and sleeve 1103*a*. The carrier 1100 may have a modular design such that different size components can be intermixed with each other, as shown in FIG. 26, to allow for a variety of packaging configurations. In some instances, the carrier 1100 may be designed to accommodate cylindrically shaped medical devices, e.g., bone screws, drill bits, bone rods, etc. The design of the cap component 1102 of the carrier 1100 may include a specific geometry on the inner surface of the cap component 1102, e.g., slits and grooves configured engage and ensure tight fixation to the packaged item, e.g., a screw or implant. When assembled as part of a packaging assembly, the carrier 1100 may be placed within a sterile barrier. Upon opening the sterile barrier, the carrier 1100 could be removed with one or more of the various methods described herein. For aseptic presentation, a medical device packaged in the carrier 1100 may be removed from the carrier by either directly attaching an instrument to an interface of a corresponding medical device (i.e., a non-touch technique) or by removing it from the carrier 1100 by squeezing the carrier and pulling out the device therefrom. In this manner, the carrier facilitates the protection of sterile barriers from sharp and pointed features and allows for the removal of the packaged item in a way that is free from contaminants.

The cap component 1102 and the sleeve component 1103 of carrier 1100 may made from a material that is transparent so that the item packaged therein is visible therethrough, as shown in FIG. 24. For example, the carrier 1100 may be made from various polymer such as, but not limited to, Mediprene 500M transparent (TPE), TM 0HET (TPE), Purell LD-PE 24 10T (LDPE), TM 9HET (TPE), and the others similar thereto. The carrier 1100 may have a thickness of between 0.4 mm and 2 mm or 0.6 mm and 10 mm. In some embodiments, the material used to make sheath 2, carrier 1100 and/or any of the other packaging components described herein may be puncture resistant and/or abrasion resistant. Additionally, some or all of the material used to make sheath 2, 102, 402, 802, 902, carrier 1100, or other components disclosed herein may be suitable for gamma irradiation and/or X-ray irradiation. In this manner, the item(s) packaged within the sheath 2, 102, 402, 802, 902 or carrier 1100 may be sterilized with gamma and/or X-ray irradiation (i.e., irradiation sterilization). This allows for the sterilization of the packaged item(s) without having to remove the same from such packaging. This is especially beneficial, for example, in the medical field as implants and tools used in medical procedures are frequently shipped, stored, and sterilized before being used. In such cases, medical personnel can utilize irradiation sterilization to sterilize a packaged item, e.g., an orthopedic implant, without having to remove the item from its packaging, e.g., a sheath or carrier.

Figure 16:
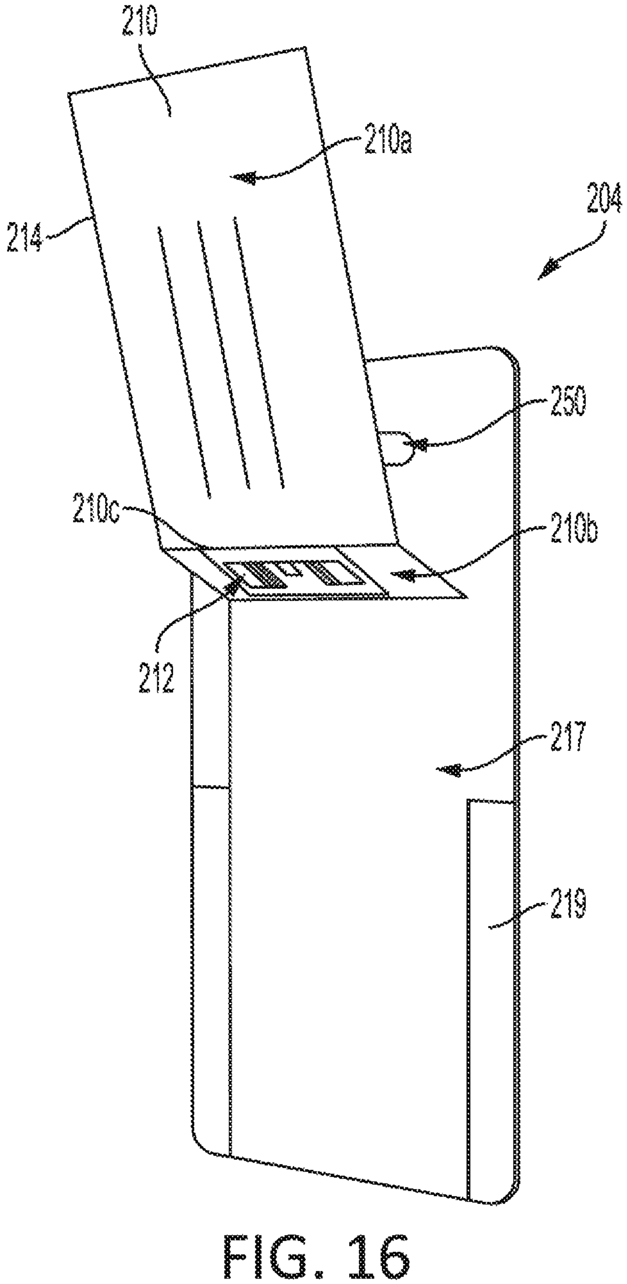
FIG. 16 is a perspective view of a base of a package assembly according to an embodiment of the present disclosure.
Figure 17:
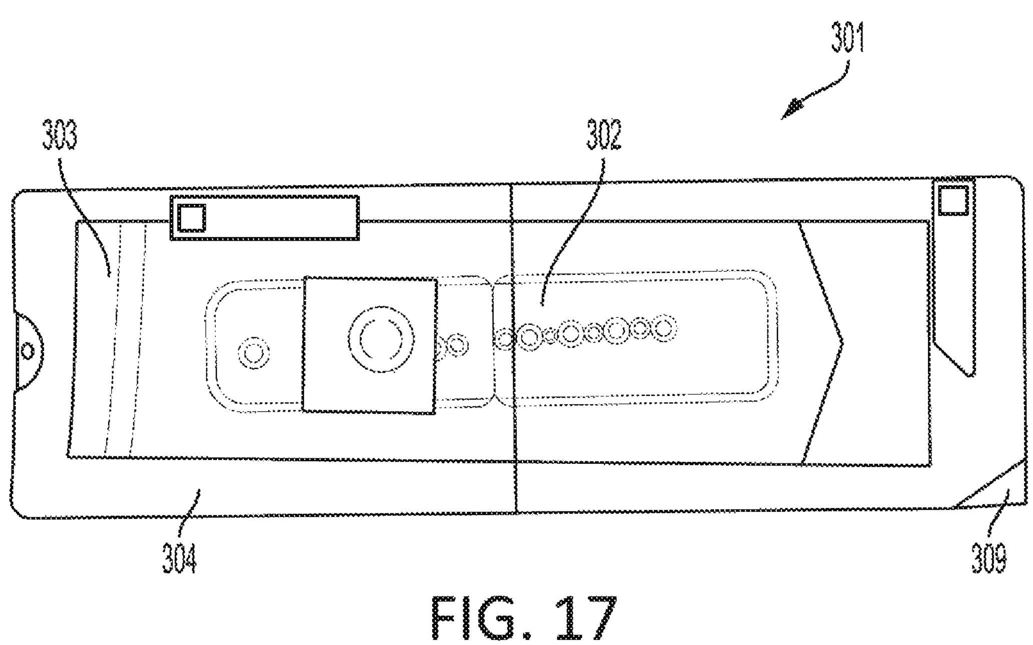
FIG. 17 is a top view of a package assembly according to an embodiment of the present disclosure.

In other embodiments, the base may include various features to facilitate shipping and storing of the implant or instrument contained a package assembly. For example, a base 204 may be as shown in FIG. 16. Base 204 has a two-layer structure that increases the surface area for printing information regarding the product associated with the package or other related information. The two-layer structure includes an information card 210 that is attached to a remainder 217 of base 204 such that an exterior-facing surface of the information card is flush or level with an exterior surface of a side portion 219 of the base surrounding the information card. The vacuum sealed pouch, e.g., pouch 3 and 103, housing the sheath is located on an opposite side of base 204 from information card 210 to limit the contact between the flexible film and the information card. Alternatively, the sealed pouch may be placed against a side of base 204 including the information card when attached to the base.

Information card 210 includes a detachable segment 210*a* and an inseparable segment 210*b* that are separated by a perforated seam 210*c*, the detachable segment has perforations 214 along three of four of its outer edges, as shown in FIG. 16, including side edges abutting side portions 219 of the base that partially surrounds the information card on opposite sides and along an edge forming part of perforated seam 210*c* such that the detachable segment can be fully detached from the inseparable segment and base 204. Inseparable segment 210*b* has perforations 214 along three of four of its side edges includes those abutting side portions 219 of the base that partially surrounds the information card and along an edge forming part of perforated seam 210*c* such that the inseparable segment may bend away from base 204 but not completely detach. In other embodiments, segment 210*b* is also detachable from a remainder of base 204, similar to segment 210*a*. In such embodiments, base 204 may include another perforation to separate segment 210*b* from base 204. Important information about product details may be printed on both the interior or exterior of information card 210. Such information may be provided in various formats, such as via bar codes, QR codes, URLs, etc. to provide digital access to such information. Additionally, through the use of digitally-retrievable information, a quantity of printed materials required on the base 204 regarding the contents of the package may be reduced. Further, the concealed surface of detachable segment 210*a* and/or inseparable segment 210*b* can be used to conceal sensitive information.

While FIG. 16 shows that detachable segment 210*a* and inseparable segment 210*b* are attached to each other, in other embodiments these segments may be separately attached to the base 204 at different locations. Additionally, information card 210 may include a tab extending from an edge thereof. It is further contemplated that base 204 may include multiple information cards that are embedded into the two-layer structure of the base. In some examples, the information cards may be embedded on opposite sides of base 204. In other examples, a base may include an embedded information card on one side of the base and a two-layer label or multi-layer label on the other side of the base. In still further examples, a two-layer label or multi-layer label may be attached to an information card. In some embodiments, the information card may have no detachable parts. In still further embodiments, the information card may have at least three detachable parts that are all divided by perforations. In such embodiments, each detachable part of the information card may contain information regarding the implant housed in the sterile barrier.

Base 204 may also include a radio frequency identification (RFID) tag 212 embedded into the two-layer structure of the base. RFID tag 212 is configured to communicate information with various RFID reader devices in either a passive or active manner. For example, the RFID may communicate information regarding shipping and storage of the package, or information related to the contents of the package and its intended use. In base 204 shown in FIG. 16, RFID tag 212 is attached to inseparable segment 210*b*. In other embodiments, the RFID may be embedded into the two-layer structure of base 204 or attached in a variety of locations, e.g., on an exterior surface of the base. In some embodiments, the RFID tag may be attached the base at a location other than that shown in FIG. 16. In yet another embodiment, the RFID may be attached to a detachable segment of the information card, e.g., detachable segment 210*a*, to allow the RFID to be removed before the information card is recycled.

The package assembly may be varied in many ways. For instance, while package assembly 1 is depicted as including a box to receive other components of the assembly, such box may, in other embodiments, be substituted with a base such as base 104 or base 204. Thus, in such alternative embodiments, package assembly 1 may include base 104 or base 204 receiving pouch 3. Similarly, in some embodiments, package assembly 101 may include box 4 in place of base 104 such that sheath 102 and pouch 103 are received in box 4.

Components of the package assemblies contemplated by the present disclosure can be made from a variety of materials. For example, the pouch may be a polyethylene (PE) peel pouch, polyamide (PA) pouch, a high-density polyethylene (HDPE) pouch (e.g., Tyvek® pouch), or a Polyethylene Terephthalate Glycol (PETG) or Polypropylene (PP) blister. In some examples, the pouch may be made of a combination of materials, such as two or more of PE, PA and HDPE. The base may be made from rigid material, for example, but not limited to, cardboard or plastic. The sheath may be made of a variety of polymers, for example, but not limited to, any type of thermoplastic polyurethane (TPU). In some embodiments, a majority of the material used in the package assemblies may be sourced from recycled material, or material that is at least recyclable or compostable. In this manner, the package assemblies described herein may be utilized in an environmentally sustainable way while still providing quality protection and sterility. These characteristics are bolstered by testing performed on the contemplated package assemblies. For example, a package assembly having a bone plate vacuum sealed within a pouch where the pouch was sealed between a flexible film and a cardboard base withstood a 1.8-meter drop test and a vibration test performed according to applicable ASTM D4169 standards.

In another aspect, the present application relates to a method of assembling the various subcomponents of package assembly 1. In one embodiment, and as shown in FIGS. 8-11, a method for packaging package assembly 1 includes inserting an implant or medical instrument, e.g., a bone screw, into sheath 2 through the open end of the sheath, i.e., unsealed portion 24. The implant, e.g., implant 28, is placed within the sheath such that the entire implant is positioned below or past the point where the curvature of the open end terminates, e.g. between reference lines 29*a* and 29*b* shown in FIG. 5. Once the implant or instrument is fully enclosed by sheath 2, sheath 2 is inserted into pouch 3 such that unsealed portion 24 of the sheath is proximate angled portion 33 of the pouch and then positioned in a central region of the pouch. After sheath 2 is positioned within pouch 3, the pouch is vacuum sealed such that end portion 34 on the pouch is sealed shut. This is done by evacuating the air within pouch 3 and then sealing end portion 34, which is preferably done with heat and pressure but could be done with an adhesive or a combination of heat and adhesive. Next, an end of pouch 3 including the end portion 34 is folded and an opposite end of pouch 3 with angled portion 33 is folded, both being folded over sheath 2. Folded pouch 3 is then inserted into box 4. Lastly, documents and/or labels containing information regarding the product are inserted into the box. Optionally, a label may be placed onto the exterior of pouch 3 prior to inserting it into box 4. Main label 7 and end-panel label 8 may be attached to box 4 at any time. Optionally, a plastic wrap or film may be applied around and enclosing the box. It is contemplated that this packaging method may be performed manually with a vacuum sealer or automatically using machinery such as a form-fill-seal automation line.

Figure 18:
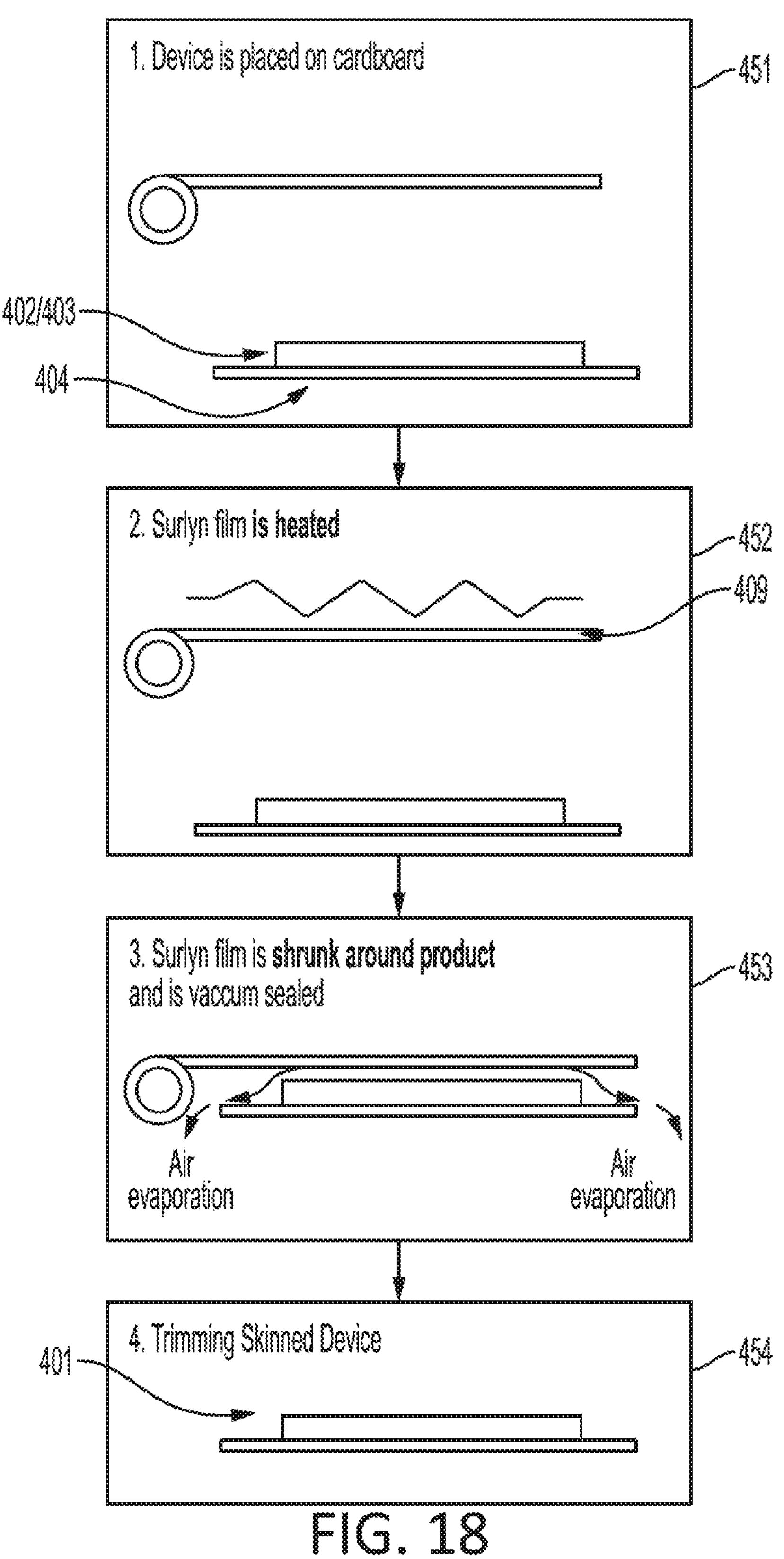
FIG. 18 is a flow chart of a process for vacuum sealing a pouch between a base and a flexible film according to an embodiment of the present disclosure.

In some method embodiments, a method for vacuum sealing a pouch and a sheath between a flexible film and a base may be as shown in FIG. 18. Specifically, vacuum sealing pouch 403 and sheath 402 between flexible film 409 and base 404 includes a first step 451 of placing the pouch housing the sheath and an implant or instrument onto the base in a central location. In a second step 452 heat is applied to the structure arranged in the first step. Then, in a third step 453, the heat causes flexible film 409 covering base 404 and pouch 403 to shrink around the pouch and form a vacuum seal of the contents between the film and the base. Optionally, in a fourth step 454, excess flexible film may be trimmed if needed.

In yet another embodiment, a method for packaging an implant into a package assembly, e.g., package assembly 1 or 101, includes steps as shown in FIG. 19. In a first step 501, the implant is inserted into a sheath, e.g., sheath 2 or 102. In a second step 502, the sheath is inserted into a vacuum sealable pouch, e.g., pouch 3 or 103. This is done by inserting the open end of the sheath, e.g., unsealed portion 24 of sheath 2, first into the open end 34 of pouch 3 such that when the sheath is fully advanced within the pouch, the open end 24 of sheath is positioned proximate the chevron seal, e.g., angled portion 33 of pouch 3, and the sheath is approximately centered within the inner chamber of the pouch. In a third step 503, the pouch is vacuum sealed such that the sheath and implant are fixed in place and immobilized with respect to the pouch. This is done by evacuating the air in the pouch and applying the final welding seal, e.g., end portion 34 of pouch 3. In a fourth step 504, the pouch is placed into an enclosure such that the pouch is surrounded by a protective barrier. If the enclosure is a box, then the pouch is disposed into a cavity of the box. Alternatively, if the enclosure is a flexible film and a base, e.g., flexible film 109 and base 104 that are sealed together and around the pouch, then placement of the pouch is such that the chevron seal of the pouch is positioned proximate the peel tab of the base, e.g., peel tab 190, as shown in FIG. 14. In a fifth step 505, the RFID tag is configured, e.g., programmed to communicate with an RFID reader device. If the RFID tag is embedded into the packaging, then configuring step 505 may optionally be completed prior to the other steps of the method.

Figure 21:
FIG. 21 is a flow diagram of a process for packaging an item in accordance with an embodiment of the present disclosure.

In some method embodiments, a method for sealing an item into a film pouch between two flexible films may be as shown in FIG. 21. In particular, this may include a flexible film base, e.g., flexible film base 903, that is formed to define a cavity having an opening in a first step 951. In a second step 952, an item for packaging, e.g., implant 956, may be inserted through the opening and placed into the cavity formed by the flexible film base. Then in a third step 953, the opening into the cavity may be covered by a flexible film, e.g., flexible film 909, and the films sealed to together to seal off the cavity. Optionally, in a final step, excess flexible film may be trimmed if needed. In some instances, this method for sealing an item within a film package and other methods described herein may be automated to provide for effective and efficient packaging.

Figure 22:
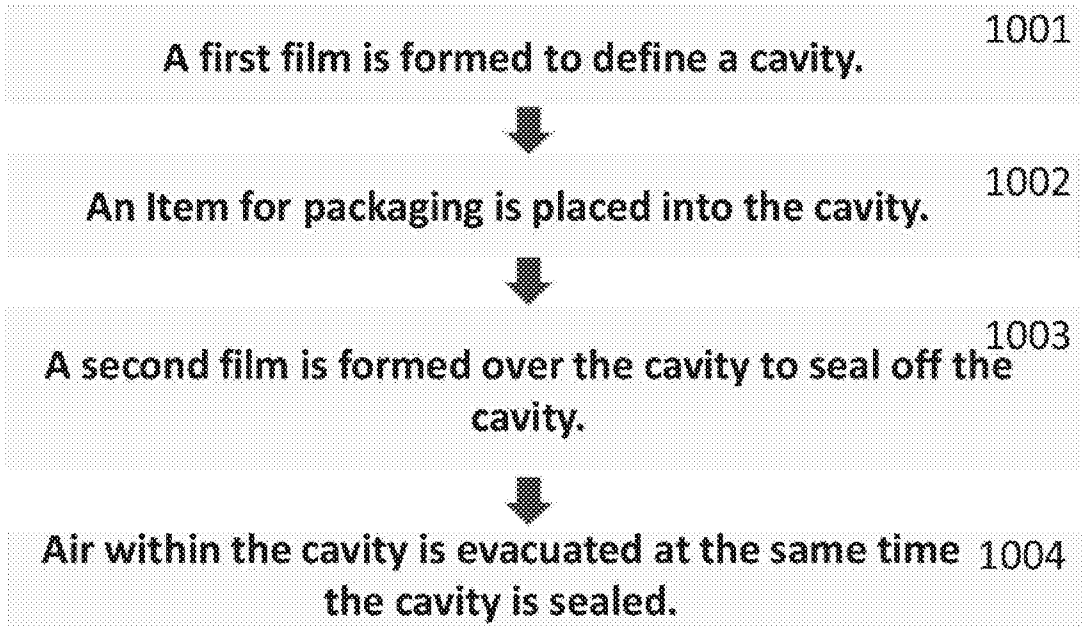
FIG. 22 is a flow chart of a process for packaging an item in accordance with an embodiment of the present disclosure.
Figure 23:
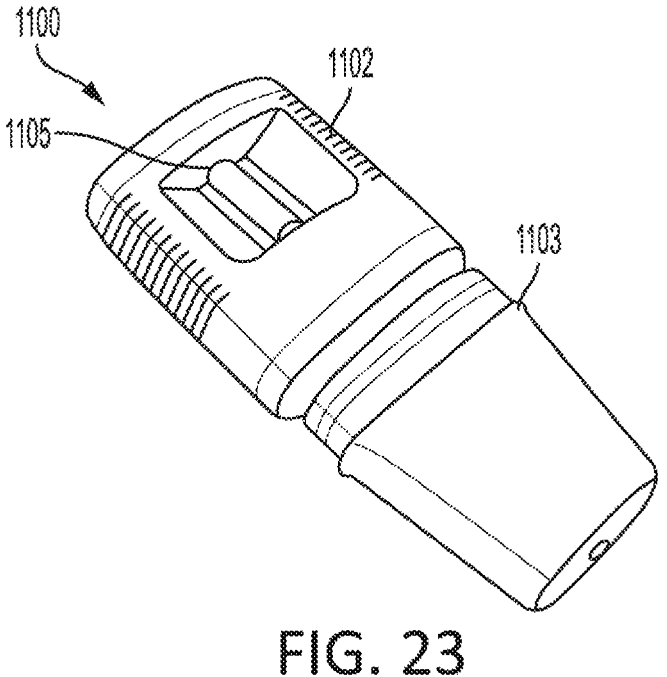
FIG. 23 is a perspective view of packaging components in accordance with an embodiment of the present disclosure.

In yet another embodiment, a method for packaging an implant into a package assembly, e.g., package assembly 909, includes steps as shown in FIG. 22. In a first step 1001, a first film, e.g., flexible film base 904, may be formed to define a cavity. In a second step 1002, an item for packaging, e.g., implant 956, is placed within the cavity. This is done by inserting the item into an opening defined by the cavity. In a third step 1003, a second film, e.g., flexible film 909, is formed over the opening of the cavity to seal off the cavity and seal the item therein. At the same time, air within the cavity is evacuated from the cavity as an additional step 1004 performed simultaneous with the third step 1003 to form a protective packaging layer around the item. Optionally, a RFID tag may be attached to the package, or embedded therein, and configured, e.g., programmed to communicate with an RFID reader device. In this manner, the packaging assembly provides a protective barrier for shipping and storing the item and facilitates tracking via the RFID tag.

Figure 12:
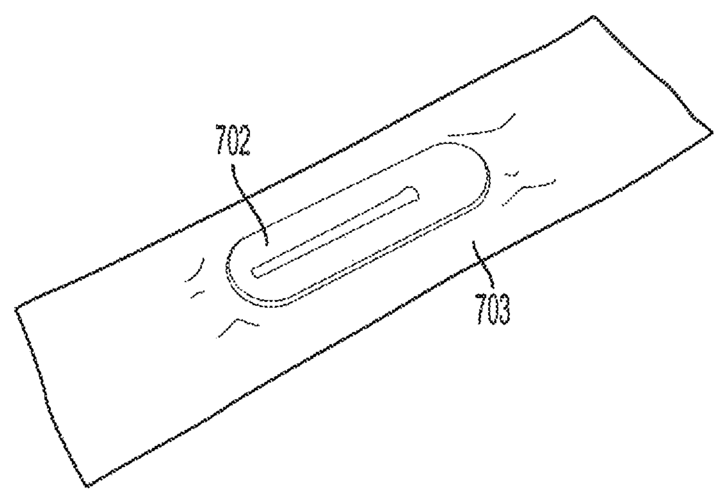
FIG. 12 is a perspective view of a pouch sealed around a sheath housing an implant according to an embodiment of the present disclosure.
Figure 13:
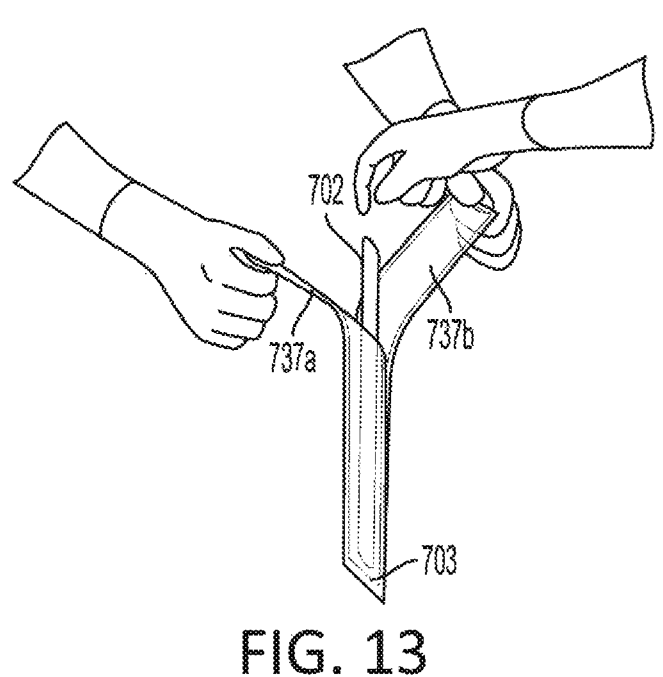
FIG. 13 is a perspective view of the pouch of FIG. 12 being peeled open.

In yet another aspect, and as shown in one example in FIGS. 12-13, a method for unpacking a sheath and implant or instrument enclosed therein from a vacuum sealed pouch includes first removing any outer packaging from around the pouch. Next, the pouch is partially torn open. This done by pulling apart the loose ends, e.g., pull tabs 37*a*, 737*a* and 37*b*, 737*b* of pouch 3, 703, of the pouch to break the seal surrounding the sheath. The seal has a portion shaped like a chevron symbol, e.g., angled portion 33 of seal 31, that allows for a gradual separation of the two layers sealed together. Lastly, once the seal has been broken and partly separated such that the sheath is exposed, the sheath is removed from the pouch, and the implant or instrument within the sheath is extracted from the sheath. Opening of the sheath may be accomplished through tearing of a perforated seam, e.g., perforations 26 of pouch 3, across the sheath structure. In this manner, the sterility of the implant or instrument may be maintained while the implant is unpacked.

In another embodiment, a method of unpacking the contents of a sheath from within a package may be performed where the package is package assembly 1 as shown in FIG. 1. In this method, after pouch 3 has been removed from box 4, pull tabs 37*a* and 37*b* are pulled apart to allow for peeling of angled portion 33 of the seal to open pouch 3 such that sheath 2 may be removed from the pouch. Then perforations 26 of sheath 2 are torn apart to extract implant 28 for the sheath. The method of unpacking may similarly be performed with package assembly 101 shown in FIGS. 14-15. In this method, an initial step involves peeling an outer film via tab 190 to expose pouch 103. Then, the remaining steps may be the same as those described for package assembly 1.

It is to be understood that the disclosure set forth herein includes any possible combinations of the particular features set forth above, whether specifically disclosed herein or not. For example, where a particular feature is disclosed in the context of a particular aspect, arrangement, configuration, or arrangement, that feature may also be used, to the extent possible, in combination with and/or in the context of other particular aspects, arrangements, configurations, and arrangements of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative arrangements and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A package comprising:

a sheath having perforations extending across the sheath such that the perforations are transverse to an elongate dimension of the sheath, the sheath configured to receive and enclose an implant or a surgical instrument;

a pouch having an inner volume receiving the sheath therein, the inner volume of the pouch being configured to be vacuum sealed;

an outer enclosure receiving the pouch, wherein the sheath has a first rigidity and the pouch has a second rigidity less than the first rigidity.

2. The package of claim 1, wherein the sheath has a thickness in a range from 0.5 mm to 3.0 mm.

3. The package of claim 1, wherein the outer enclosure includes a backing board and a film that are sealed together with a seal that extends around the pouch disposed between the backing board and the film.

4. The package of claim 3, wherein the seal is formed through heat connecting the film onto the board.

5. The package of claim 3, wherein the backing board is paperboard.

6. The package of claim 1, wherein the backing board includes a first layer and a second layer, each layer being substantially planar.

7. The package of claim 6, wherein the first layer includes an information card that is at least partially detachable from the second layer.

8. The package of claim 6, further comprising a radio frequency identification (RFID) tag on the first layer.

9. The package of claim 8, wherein the RFID tag is a passive RFID tag.

10. The package of claim 6, wherein the first layer is joined to a remainder of the plurality of planar layers via a line of perforations that define an outer perimeter of the first layer.

11. The package of claim 1, wherein a top layer and of a bottom layer of the sheath are unattached at one end of the sheath, such unattached end defining an opening, and wherein the perforations extend across a width of the sheath.

12. The package of the claim 1, wherein the pouch is made of polyethylene (PE) film, high-density polyethylene (HDPE) film, or polyamide (PA) film.

13. The package of claim 1, wherein the pouch includes two film layers attached together with a peelable seal.

14. The package of claim 3, wherein the film includes a peel tab that extends beyond an edge of the backing board.

15. The package of claim 1, wherein the outer enclosure is a box and a film wrapped around the box.

16. A system for packaging an object for use in surgery comprising:

the object;

a sheath having an enclosed pocket with the object disposable therein, the sheath having a line of perforations extending from a first side of the enclosed pocket to a second side of the enclosed pocket opposite the first side; and a pouch enclosing the sheath and the object, the pouch having a vacuum sealed periphery including a sealed portion with an apex shape configured to be peeled open, wherein the sheath has a first thickness and the pouch has a second thickness less than the first thickness.

17. The system of claim 16, wherein the sheath includes an elongate dimension extending from a first end to a second end and the first and second ends both have a rounded shape.

18. The system of claim 16, wherein the enclosed pocket is defined by two layers of the sheath and one layer of the two layers has a cutout at one end of an elongate dimension of the sheath to define a tab for separating the two layers.

19. The system of claim 16, wherein the sheath includes a first recess along the first side and a second recess along the second side, each of the first and second recesses being positioned adjacent to respective ends of the line of perforations extending across the enclosed pocket.

20. The system of claim 19, wherein the first and second recesses are V-shaped.

* * * * *